US012790287B2

(12) United States Patent
Ohgata et al.

(10) Patent No.: US 12,790,287 B2
(45) Date of Patent: *Nov. 10, 2026

(54) 3,5,5-TRIMETHYLHEXANOIC ACID COMPOSITION, METHOD FOR PRODUCING THE COMPOSITION AND METHOD FOR IMPROVING SULFURIC ACID COLORING OF THE COMPOSITION

(71) Applicant: KH Neochem Co., Ltd., Tokyo (JP)

(72) Inventors: Yusuke Ohgata, Ichihara (JP); Kouji Kitabatake, Ichihara (JP); Ryuta Kawabe, Ichihara (JP)

(73) Assignee: KH NEOCHEM CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/870,257

(22) PCT Filed: Mar. 19, 2024

(86) PCT No.: PCT/JP2024/010655

§ 371 (c)(1),
(2) Date: Nov. 27, 2024

(87) PCT Pub. No.: WO2024/219139

PCT Pub. Date: Oct. 24, 2024

(65) Prior Publication Data

US 2025/0162972 A1 May 22, 2025

(30) Foreign Application Priority Data

Apr. 21, 2023 (JP) ................................ 2023-070014

(51) Int. Cl.
*C07C 53/128* (2006.01)
*A61K 8/36* (2006.01)

(52) U.S. Cl.
CPC .............. *C07C 53/128* (2013.01); *A61K 8/36* (2013.01); *A61K 2800/10* (2013.01)

(58) Field of Classification Search
CPC ................................ C07C 53/128; A61K 8/36
USPC ........................................................ 562/606
See application file for complete search history.

(56) References Cited

U.S. PATENT DOCUMENTS

| | | | |
|---|---|---|---|
| 2,470,859 | A | 5/1949 | Pavlic |
| 4,619,790 | A | 10/1986 | Kummer et al. |
| 2019/0194108 | A1 | 6/2019 | Sang et al. |
| 2020/0392062 | A1 | 12/2020 | Kucmierczyk et al. |
| 2024/0025831 | A1 | 1/2024 | Kishimoto et al. |

FOREIGN PATENT DOCUMENTS

| | | | |
|---|---|---|---|
| JP | S6058900 | B2 | 12/1985 |
| JP | 2019112392 | A | 7/2019 |
| JP | 2020200327 | A | 12/2020 |
| WO | WO-2022118917 | A1 | 6/2022 |

OTHER PUBLICATIONS

Japanese Office Action for Japanese Application No. 2023-070014, dated Jun. 27, 2023, 6 pages.

Chemical Book 3,5,5-trimethylhexanoic asid, 4 pages, https://www.chemicalbook.com/ChemicalProductProperty_JP_CB8170213.htm#:~:text=3%2C5%2C5-Trimethylhexanoic%20acid%2C%20is%20an%20important%20organic%20intermediate.%20It,Used%20in%20organic%20Synthesis%2C%20pharmaceuticals%2C%20agrochemicals%20and%20dyestuff (2017).

International Search Report of International Application No. PCT/JP2024/010655, Japan Patent Office, mailed on May 14, 2024, 7 pages.

Japanese Office Action for Japanese Application No. 2023-070014, dated Jun. 20, 2023, 6 pages.

Sang, R., et al., "Palladium-Catalyzed Selective Generation of CO from Formic Acid for Carbonylation of Alkenes," Journal of the American Chemical Society, 140:5217-5223; S1-S21, American Chemical Society, United States (Apr. 2018).

*Primary Examiner* — Ana Z Muresan
(74) *Attorney, Agent, or Firm* — HSML P.C.

(57) ABSTRACT

A 3,5,5-trimethylhexanoic acid composition containing 3,5,5-trimethylhexanoic acid and t-butyl alcohol in which the t-butyl alcohol concentration in terms of toluene-d8 measured by gas chromatography-olfactometry/mass spectrometry.

11 Claims, No Drawings

3,5,5-TRIMETHYLHEXANOIC ACID COMPOSITION, METHOD FOR PRODUCING THE COMPOSITION AND METHOD FOR IMPROVING SULFURIC ACID COLORING OF THE COMPOSITION

TECHNICAL FIELD

The technique of the present disclosure relates to a 3,5,5-trimethylhexanoic acid composition, a method for producing the composition and a method for improving sulfuric acid coloring of the composition.

BACKGROUND ART

It is known that 3,5,5-trimethylhexanoic acid can be synthesized by oxidation of 3,5,5-trimethylhexanal, which is a precursor aldehyde (for example, see PTL 1).

3,5,5-Trimethylhexanoic acid is sometimes used as a raw material of a resin, a cosmetic product, a refrigeration oil or the like but is colored during the synthesis of the resin, the preparation of the cosmetic product, the preparation of the refrigeration oil or the like. Such coloring during the synthesis or during the preparation can be observed by a sulfuric coloring (sulfuric acid coloring) test, and impurities such as aldehydes are known to affect the deterioration of the sulfuric coloring evaluation.

CITATION LIST

Patent Literature

PTL 1: WO 2022/118917

SUMMARY OF INVENTION

Technical Problem

Even when 3,5,5-trimethylhexanoic acid is purified by distillation to reduce the impurities such as an aldehyde, in order to suppress the coloring during the synthesis of a resin, the preparation of a cosmetic product, the preparation of a refrigeration oil or the like, the deterioration of the sulfuric acid coloring evaluation (coloring in a sulfuric acid coloring test) is still observed.

The technique of the present disclosure was made under the above circumstances. A problem of the technique of the present disclosure is to provide a 3,5,5-trimethylhexanoic acid composition which is excellent in sulfuric acid coloring evaluation, a method for producing the composition and a method for improving sulfuric acid coloring of the composition, and an aim thereof is to solve the problem.

Solution to Problem

<1> A 3,5,5-trimethylhexanoic acid composition containing 3,5,5-trimethylhexanoic acid and t-butyl alcohol, in which the t-butyl alcohol concentration in terms of toluene-d8 measured by gas chromatography-olfactometry/mass spectrometry under the conditions below exceeds 0 ppb by volume and is 200 ppb by volume or less:

Measurement Conditions the 3,5,5-trimethylhexanoic acid composition in an amount of 5.0 g is filled into a sealable 500-mL container and left still at 30° C. for 20 minutes or more. Then, 200 mL of the gas phase is sucked, and the residue after removing $H_2O$, $N_2$, $O_2$ and $CO_2$ is concentrated with a concentrator, and the concentrated sample is measured by gas chromatography-olfactometry under the conditions below, and the structure of a measured component is analyzed with a mass spectrometry detector:

Analysis column: a column using dimethylpolysiloxane as a stationary phase; a length of 60 m×an inner diameter of 320 μm×a film thickness of 1 μm Heating program: After maintaining at 35° C. for two minutes, the temperature is increased at 10° C./minute, and the temperature is maintained for seven minutes and 30 seconds after the temperature reaches 240° C.

Carrier gas: helium

The measurement conditions of the mass spectrometry detector are as follows.

Ionization mode: EI
Measurement type: scan
Ion source temperature: 250° C.
Quadrupole temperature: 150° C.
Electron energy: 70.0 eV
Initial mass of scanning: 30
Final mass of scanning: 400

<2> The 3,5,5-trimethylhexanoic acid composition according to <1> which is used for a cosmetic product.

<3> The 3,5,5-trimethylhexanoic acid composition according to <1> which is used for a refrigeration oil.

<4> A method for producing a 3,5,5-trimethylhexanoic acid composition having a synthesis step of synthesizing 3,5,5-trimethylhexanal by hydroformylation reaction of diisobutylene and oxo gas and synthesizing crude 3,5,5-trimethylhexanoic acid by subsequent oxidation reaction, and a purification step of purifying the crude 3,5,5-trimethylhexanoic acid, in which the purification step includes a distillation step of distilling the crude 3,5,5-trimethylhexanoic acid, a water washing step of washing the 3,5,5-trimethylhexanoic acid obtained in the distillation step with water and a bubbling step of bubbling the 3,5,5-trimethylhexanoic acid obtained in the water washing step with an inert gas.

<5> A method for increasing sulfuric acid coloring evaluation of a 3,5,5-trimethylhexanoic acid composition, which is a method for improving sulfuric acid coloring of a 3,5,5-trimethylhexanoic acid composition containing 3,5,5-trimethylhexanoic acid and t-butyl alcohol, in which the t-butyl alcohol concentration in terms of toluene-d8 measured by gas chromatography-olfactometry/mass spectrometry under the conditions below is adjusted to exceed 0 ppb by volume and to be 200 ppb by volume or less:

Measurement Conditions the 3,5,5-trimethylhexanoic acid composition in an amount of 5.0 g is filled into a sealable 500-mL container and left still at 30° C. for 20 minutes or more. Then, 200 mL of the gas phase is sucked, and the residue after removing $H_2O$, $N_2$, $O_2$ and $CO_2$ is concentrated with a concentrator, and the concentrated sample is measured by gas chromatography-olfactometry under the conditions below, and the structure of a measured component is analyzed with a mass spectrometry detector:

Analysis column: a column using dimethylpolysiloxane as a stationary phase; a length of 60 m×an inner diameter of 320 μm×a film thickness of 1 μm Heating program: After maintaining at 35° C. for two minutes, the temperature is increased at 10° C./minute, and the temperature is maintained for seven minutes and 30 seconds after the temperature reaches 240° C.

Carrier gas: helium

The measurement conditions of the mass spectrometry detector are as follows.

Ionization mode: EI

Measurement type: scan

Ion source temperature: 250° C.

Quadrupole temperature: 150° C.

Electron energy: 70.0 eV

Initial mass of scanning: 30

Final mass of scanning: 400.

Advantageous Effects of Invention

According to the technique of the present disclosure, a 3,5,5-trimethylhexanoic acid composition which is excellent in sulfuric acid coloring evaluation, a method for producing the composition and a method for improving sulfuric acid coloring of the composition can be provided.

DESCRIPTION OF EMBODIMENTS

Any upper limit value and any lower limit value of the numerical ranges described in this description can be combined. For example, when "A to B" and "C to D" are described as numerical ranges, the numerical ranges of "A to D" and "C to B" are also included in the scope of the present disclosure.

In addition, the numerical range "a lower limit value to an upper limit value" described in this description means the lower limit value or more and the upper limit value or less, unless otherwise specified.

3,5,5-Trimethylhexanoic Acid Composition

The 3,5,5-trimethylhexanoic acid composition according to the embodiment is a 3,5,5-trimethylhexanoic acid composition containing 3,5,5-trimethylhexanoic acid and t-butyl alcohol, and the t-butyl alcohol concentration in terms of toluene-d8 measured by gas chromatography-olfactometry/mass spectrometry under the conditions below exceeds 0 ppb by volume and is 200 ppb by volume or less.

Measurement Conditions

The 3,5,5-trimethylhexanoic acid composition in an amount of 5.0 g is filled into a sealable 500-mL container and left still at 30° C. for 20 minutes or more. Then, 200 mL of the gas phase is sucked, and the residue after removing $H_2O$, $N_2$, $O_2$ and $CO_2$ is concentrated with a concentrator.

The concentrated sample is measured by gas chromatography-olfactometry under the conditions below, and the structure of a measured component is analyzed with a mass spectrometry detector.

Analysis column: a column using dimethylpolysiloxane as a stationary phase; a length of 60 m×an inner diameter of 320 μm×a film thickness of 1 μm Heating program: After maintaining at 35° C. for two minutes, the temperature is increased at 10° C./minute, and the temperature is maintained for seven minutes and 30 seconds after the temperature reaches 240° C.

Carrier gas: helium

The measurement conditions of the mass spectrometry detector are as follows.

Ionization mode: EI

Measurement type: scan

Ion source temperature: 250° C.

Quadrupole temperature: 150° C.

Electron energy: 70.0 eV

Initial mass of scanning: 30

Final mass of scanning: 400

The sulfuric acid coloring is sometimes referred to as "sulfuric coloring" below.

The impurities contained in a 3,5,5-trimethylhexanoic acid composition have been believed to be aldehydes such as 3,5,5-trimethylhexanal, and the impurities have been removed by distilling the 3,5,5-trimethylhexanoic acid composition. Impurities have not been observed at the detection level from a 3,5,5-trimethylhexanoic acid composition purified by distillation by general gas chromatography (GC). Nevertheless, coloring has been observed in sulfuric acid coloring evaluation.

As a result of extensive examination on the cause of the coloring, it was found through gas chromatography-olfactometry with a higher sensitivity that a very small amount of t-butyl alcohol (t-BuOH) exists in a 3,5,5-trimethylhexanoic acid composition.

It was also found that, although coloring of t-BuOH alone is not observed in sulfuric acid coloring evaluation, the sulfuric acid coloring evaluation deteriorates when t-BuOH is contained in a 3,5,5-trimethylhexanoic acid composition. That is, it was found that the existence of t-BuOH, which has not been recognized as an impurity, deteriorates the sulfuric acid coloring evaluation of the 3,5,5-trimethylhexanoic acid composition.

The present invention solves the novel problem (the deterioration of the sulfuric acid coloring evaluation due to the existence of t-BuOH) by forming the 3,5,5-trimethylhexanoic acid composition with the above configuration.

Gas Chromatography-Olfactometry/Mass Spectrometry

The gas chromatography-olfactometry/mass spectrometry is conducted by concentrating the sample by the method below and then analyzing a component of the concentrated sample by gas chromatography-olfactometry while analyzing the structure of the component with a mass spectrometry detector.

Concentration of Sample

The 3,5,5-trimethylhexanoic acid composition is a liquid at atmospheric pressure (0.1 MPa) at room temperature (25° C.). The 3,5,5-trimethylhexanoic acid composition in an amount of 5.0 g is filled into a sealable 500-mL container and left still at 30° C. for 20 minutes or more. Then, 200 mL of the gas phase is sucked, and the residue after removing $H_2O$, $N_2$, $O_2$ and $CO_2$ is concentrated with a concentrator.

The concentrator may be a stand-alone type or may be connected to a gas chromatography-olfactometry/mass spectrometry detector.

As the concentrator, for example, "Entech7200 automated concentrator" manufactured by ENTECH INSTRUMENTS can be used.

The concentration conditions are as follows.

Internal standard substance: 100 mL (standard toluene-d8 gas: concentration of 10 ppb by volume, nitrogen as a dilution gas, Sumitomo Seika Chemicals Company, Limited.)

Concentration method: CTD mode (Cold Trap Dehydration)

Temperature condition of Dehydration Module 1 (Empty Trap: a ceramic-coated trap without adsorbent filling): Trap Temp. −40° C., Desorption Temp. 0° C.

Temperature condition of Cold Tenax (registered trademark) Module 2 (Tenax TA Trap: a ceramic-coated trap filled with Tenax TA as an adsorbent): Trap Temp. −30° C., Desorption Temp. 200° C.

Temperature condition of Focusing Module 3 (Cryo focusing): Trap Temp. −165° C., Desorption Temp. 100° C.

Sample flow rate: 50 mL/min.

He Flush Volume: 75 mL

M1 to M2 Volume: 40 mL (100 mL/min)

M2 to M3 Time: 3.0 min

Injection time: 0.3 min

Here, Tenax TA is low polarity porous polymer beads using 2,6-diphenyl-p-phenylene oxide as a base.

M1, M2 and M3 correspond to Modules 1, 2 and 3, respectively, and "M1 to M2" and "M2 to M3" show the conditions of the sample flows between the Modules. The following procedures are conducted in the respective Modules.

M1: removal of water, air and the like

M2: removal of VOC by causing $CO_2$ to pass through

M3: focusing of the sample

Gas Chromatography-Olfactometry

As the gas chromatography-olfactometry (GC-olfactometry) apparatus, for example, "Agilent 7890B gas chromatography system" manufactured by Agilent Technologies can be used.

The measurement conditions of the GC-olfactometry are as follows.

Analysis column: DB-1 manufactured by Agilent Technologies (a column using dimethylpolysiloxane as a stationary phase; a length of 60 m×an inner diameter of 320 μm×a film thickness of 1 μm)

Heating program: After maintaining at 35° C. for two minutes, the temperature is increased at 10° C./minute, and the temperature is maintained for seven minutes and 30 seconds after the temperature reaches 240° C.

Carrier gas: helium

Control mode: constant pressure (153.09 kPa)

The concentrated sample is separated by a capillary column and then sent to ODP3 (sniffing port) and a mass spectrometry detector (for example, MSD5977B below) at a ratio of

Mass Spectrometry Detector

As the mass spectrometry detector (MSD), for example, "Agilent 5977B MSD" manufactured by Agilent Technologies can be used.

The measurement conditions of the MSD are as follows.

Ionization mode: EI

Measurement type: scan

Ion source temperature: 250° C.

Quadrupole temperature: 150° C.

Electron energy: 70.0 eV

Initial mass of scanning: 30

Final mass of scanning: 400

Calibration curve: created using standard toluene-d8 gas manufactured by Sumitomo Seika Chemicals Company, Limited. (concentration: 10 ppb by volume, dilution gas: nitrogen).

For the data analysis, an extracted ion chromatogram (EIC) is used, and the EIC peak area of t-butyl alcohol (EIC: m/z 59.000) that appears in the relative retention time of 0.48 to 0.56 is observed, where the relative retention time of toluene-d8 is regarded as 1.0.

The t-butyl alcohol concentration in terms of toluene-d8 of the 3,5,5-trimethylhexanoic acid vapor is calculated using an equation derived from the calibration curve, "concentration in terms of toluene-d8 (ppb by volume)=$3.49\times10^{-6}\times$ EIC peak area", where the sensitivity of the EIC peak of t-butyl alcohol and the sensitivity of the EIC peak of toluene-d8 are supposed to be equal.

t-Butyl Alcohol Concentration in Terms of Toluene-d8

The t-butyl alcohol concentration in terms of toluene-d8 of the 3,5,5-trimethylhexanoic acid composition according to the embodiment measured by the GC-olfactometry/MSD is preferably 190 ppb by volume or less, more preferably 160 ppb by volume or less, further preferably 140 ppb by volume or less.

Sulfuric Acid Coloring Evaluation

The sulfuric acid coloring evaluation of the 3,5,5-trimethylhexanoic acid composition according to the embodiment is conducted by the method below.

After 40 mL of a sample is put in a container and stirred in an ice bath for three minutes, 0.2 mL of concentrated sulfuric acid (for color test with sulfuric acid) is further added, and the mixture is stirred in an ice bath for one minute. Next, the container is placed in a water bath and left still at 20° C. for five minutes. Then, the Hazen unit color number (APHA) of the sample is measured with a spectrophotometric colorimeter (for example, "SE7700" manufactured by NIPPON DENSHOKU INDUSTRIES Co., Ltd.). In the measurement, the average value of the results of three measurements of the same sample is calculated and used as the score of the Hazen unit color number.

Method for Producing 3,5,5-Trimethylhexanoic Acid Composition

The method for producing a 3,5,5-trimethylhexanoic acid composition according to the embodiment is not particularly restricted but preferably has a synthesis step of synthesizing crude 3,5,5-trimethylhexanoic acid and a purification step of purifying the crude 3,5,5-trimethylhexanoic acid. The purification step preferably includes a water washing step of washing the crude 3,5,5-trimethylhexanoic acid with water and a bubbling step of bubbling the 3,5,5-trimethylhexanoic acid obtained in the water washing step with an inert gas.

Synthesis Step

The crude 3,5,5-trimethylhexanoic acid may be synthesized by a known synthesis method.

For example, the crude 3,5,5-trimethylhexanoic acid can be synthesized by the method described in WO2022/118917. Specifically, for example, 3,5,5-trimethylhexanal is synthesized by hydroformylation reaction of diisobutylene and oxo gas, and crude 3,5,5-trimethylhexanoic acid is synthesized by subsequent oxidation reaction.

Purification Step

The purification step includes a water washing step of washing the crude 3,5,5-trimethylhexanoic acid with water and a bubbling step of bubbling the 3,5,5-trimethylhexanoic acid obtained in the water washing step with an inert gas.

The purification step may further include a distillation step.

Distillation Step

In the distillation step, for example, the crude 3,5,5-trimethylhexanoic acid is put into a three-neck flask having a reflux condenser and a thermometer and distilled at a reduced pressure of 25 kPa, and the fraction of the temperature at the top of the tower of 184 to 191° C. is collected.

Water Washing Step

The water washing step is a step of washing the crude 3,5,5-trimethylhexanoic acid with water.

The water washing step is a step of mixing the crude 3,5,5-trimethylhexanoic acid obtained in the synthesis step and water and, after phase separation into an aqueous layer and an organic layer, obtaining the organic layer containing 3,5,5-trimethylhexanoic acid.

The water washing step is preferably conducted after the distillation step.

The amount of the water used is preferably 10 to 300 parts by mass, more preferably 20 to 200 parts by mass, based on 100 parts by mass of the crude 3,5,5-trimethylhexanoic acid in view of the efficiency of extraction. When water is mixed with the crude 3,5,5-trimethylhexanoic acid, the temperature is not particularly limited but is preferably a temperature between 5 to 80° C., more preferably a temperature between 10 to 50° C., further preferably a temperature between 35 to 50° C., in view of the efficiency of extraction.

The crude 3,5,5-trimethylhexanoic acid and water can be mixed, for example, by a batch process, a continuous process or the like.

In the case of a batch process, examples thereof include a method of putting the crude 3,5,5-trimethylhexanoic acid and water into a mixing tank, stirring preferably for 10 seconds to two hours, then leaving still preferably for one minute to two hours for phase separation and obtaining the organic layer containing 3,5,5-trimethylhexanoic acid. An operation of further adding water to the obtained organic layer containing 3,5,5-trimethylhexanoic acid and obtaining the organic layer containing 3,5,5-trimethylhexanoic acid after phase separation may be repeated, and the operation is repeated preferably once to three times. In this case, the addition amount of the water used is preferably 10 to 300 parts by mass based on 100 parts by mass of the crude 3,5,5-trimethylhexanoic acid per one operation.

As the apparatus for conducting by a continuous process, an apparatus which is generally used for continuous extraction or the like, such as a combination of a mixer and a settler, a spray tower, a packed tower and a tray tower, can be used, but in particular, a packed tower or a tray tower having a theoretical tray number of three or more is preferably used.

Bubbling Step

The bubbling step is a step of bubbling the 3,5,5-trimethylhexanoic acid obtained in the water washing step with an inert gas.

The organic layer containing 3,5,5-trimethylhexanoic acid obtained in the water washing step is bubbled with an inert gas to remove water and t-BuOH.

As the inert gas, for example, nitrogen gas can be used.

The amount of the inert gas introduced for bubbling is preferably 0.5 to 15 l/min, more preferably 2.5 to 7.5 l/min per 1 kg of the organic layer. The temperature of the bubbling step is 40° C. or higher and 80° C. or lower, and the bubbling time is generally one to 30 hours, preferably five to 15 hours.

Method for Improving Sulfuric Acid Coloring of 3,5,5-Trimethylhexanoic Acid Composition The method for improving sulfuric acid coloring of a 3,5,5-trimethylhexanoic acid composition according to the embodiment is a method for improving sulfuric acid coloring of a 3,5,5-trimethylhexanoic acid composition containing 3,5,5-trimethylhexanoic acid and t-butyl alcohol, and the t-butyl alcohol concentration in terms of toluene-d8 measured by gas chromatography-olfactometry/mass spectrometry under the conditions above is adjusted to exceed 0 ppb by volume and to be 200 ppb by volume or less.

The "method for improving sulfuric acid coloring of a 3,5,5-trimethylhexanoic acid composition according to the embodiment" is sometimes simply referred to as "the method for improving sulfuric acid coloring according to the embodiment" below.

According to the method for improving sulfuric acid coloring according to the embodiment, by adjusting the t-BuOH concentration of the 3,5,5-trimethylhexanoic acid composition to 200 ppb by volume or less, coloring of the 3,5,5-trimethylhexanoic acid composition can be suppressed in a sulfuric acid coloring test, and the sulfuric acid coloring evaluation can be improved. The sulfuric acid coloring evaluation is made based on the Hazen unit color number (APHA), and the specific method for evaluation is as described above.

The t-BuOH concentration of the 3,5,5-trimethylhexanoic acid composition is preferably 190 ppb by volume or less, more preferably 160 ppb by volume or less, further preferably 140 ppb by volume or less.

EXAMPLES

Next, the technique of the present disclosure will be specifically explained referring to Examples, but the technique of the present disclosure is not restricted by these examples.

Example 1

(Synthesis Step)

Crude 3,5,5-trimethylhexanoic acid was synthesized referring to the method described in WO2022118917A1. That is, 3,5,5-trimethylhexanal was synthesized by hydroformylation reaction of diisobutylene and oxo gas, and crude 3,5,5-trimethylhexanoic acid was obtained by subsequent oxidation reaction.

(Distillation Step)

Next, 239.50 g of the crude 3,5,5-trimethylhexanoic acid was put into a 300-mL three-neck flask having a reflux condenser and a thermometer and distilled at a reduced pressure of 25 kPa, and the fraction of the temperature at the top of the tower of 184 to 191° C. was collected. Thus, 190.28 g of 3,5,5-trimethylhexanoic acid was obtained with a recovery rate of 79.4%.

(Water Washing Step)

Next, 190 g of the 3,5,5-trimethylhexanoic acid after the distillation step and 211 g of water were put into a 1-L glass sample bottle, stirred by shaking at a temperature of 50° C. for one minute and then left still for 30 minutes to separate the phases into an aqueous layer and an organic layer.

(Bubbling Step)

Next, the organic layer after the water washing step was put into a short-neck flask, and by introducing nitrogen at a flow rate of 800 mL/minute through a sparger at a temperature of 50° C. and stirring for eight hours, 188 g of a 3,5,5-trimethylhexanoic acid composition was obtained.

As a result of gas chromatography mass spectrometry with a concentrator of the obtained 3,5,5-trimethylhexanoic acid composition under the conditions described below, the t-butyl alcohol concentration in terms of toluene-d8 was 185 ppb by volume.

A sulfuric coloring test of the obtained 3,5,5-trimethylhexanoic acid composition was conducted by the method described below, and the Hazen unit color number was 32.

Example 2

The same procedures as those in Example 1 were conducted except that the water washing step was conducted twice and that the bubbling step was conducted for 10 hours.

As a result of gas chromatography mass spectrometry with a concentrator of the obtained 3,5,5-trimethylhexanoic acid composition under the conditions described below, the t-butyl alcohol concentration in terms of toluene-d8 was 144 ppb by volume.

A sulfuric coloring test of the obtained 3,5,5-trimethylhexanoic acid composition was conducted by the method described below, and the Hazen unit color number was 24.

Example 3

The same procedures as those in Example 1 were conducted except that the water washing step was conducted three times and that the bubbling step was conducted for 7.5 hours.

As a result of gas chromatography mass spectrometry with a concentrator of the obtained 3,5,5-trimethylhexanoic acid composition under the conditions described below, the t-butyl alcohol concentration in terms of toluene-d8 was 108 ppb by volume.

A sulfuric coloring test of the obtained 3,5,5-trimethylhexanoic acid composition was conducted by the method described below, and the Hazen unit color number was 24.

Comparative Example 1

The same procedures as those in Example 1 were conducted except that the water washing step and the bubbling step were not conducted.

As a result of gas chromatography mass spectrometry with a concentrator of the obtained 3,5,5-trimethylhexanoic acid composition under the conditions described below, the t-butyl alcohol concentration in terms of toluene-d8 was 317 ppb by volume.

A sulfuric coloring test of the obtained 3,5,5-trimethylhexanoic acid composition was conducted by the method described below, and the Hazen unit color number was 94.

Gas Chromatography-Olfactometry/Mass Spectrometry

The gas chromatography-olfactometry/mass spectrometry of the 3,5,5-trimethylhexanoic acid compositions obtained in Examples 1 to 3 and Comparative Example 1 was conducted under the conditions below.

Concentration of Sample

First, each 3,5,5-trimethylhexanoic acid composition obtained was concentrated using the concentrator below under the conditions below.

Concentrator: Entech7200 automated concentrator manufactured by ENTECH INSTRUMENTS Sample amount: 5.0 g Container volume: 500 mL Injection amount: 200 mL of the gas phase in the container left still at 30° C. for 20 minutes or more Internal standard substance: 100 mL (standard toluene-d8 gas: concentration of 10 ppb by volume, nitrogen as a dilution gas, Sumitomo Seika Chemicals Company, Limited.)

Concentration method: CTD mode (Cold Trap Dehydration)

Temperature condition of Dehydration Module 1 (Empty Trap: a ceramic-coated trap without adsorbent filling): Trap Temp. −40° C., Desorption Temp. 0° C.

Temperature condition of Cold Tenax (registered trademark) Module 2 (Tenax TA Trap: a ceramic-coated trap filled with Tenax TA as an adsorbent): Trap Temp. −30° C., Desorption Temp. 200° C.

Temperature condition of Focusing Module 3 (Cryo focusing): Trap Temp. −165° C., Desorption Temp. 100° C.

Sample flow rate: 50 mL/min

He Flush Volume: 75 mL

M1 to M2 Volume: 40 mL (100 mL/min)

M2 to M3 Time: 3.0 min

Injection time: 0.3 min

Here, Tenax TA is low polarity porous polymer beads using 2,6-diphenyl-p-phenylene oxide as a base.

Next, gas chromatography-olfactometry/mass spectrometry of the concentrated sample was conducted using the gas chromatography-olfactometry (GC-olfactometry) apparatus and the mass spectrometry detector (MSD) below.

GC-Olfactometry

Measurement device: Agilent 7890B gas chromatography system manufactured by Agilent Technologies Analysis column: DB-1 manufactured by Agilent Technologies (a column using dimethylpolysiloxane as a stationary phase; a length of 60 m×an inner diameter of 320 μm×a film thickness of 1 μm)

Heating program: After maintaining at 35° C. for two minutes, the temperature is increased at 10° C./minute, and the temperature is maintained for seven minutes and 30 seconds after the temperature reaches 240° C.

Carrier gas: helium

Control mode: constant pressure (153.09 kPa)

The concentrated sample is separated by a capillary column and then sent to ODP3 (sniffing port) and MSD5977B at a ratio of 1/1.

MSD

Detector: Agilent 5977B MSD manufactured by Agilent Technologies

Ionization mode: EI
Measurement type: scan
Ion source temperature: 250° C.
Quadrupole temperature: 150° C.
Electron energy: 70.0 eV
Initial mass of scanning: 30
Final mass of scanning: 400
Calibration curve: created using standard toluene-d8 gas manufactured by Sumitomo Seika Chemicals Company, Limited. (concentration: 10 ppb by volume, dilution gas: nitrogen).

Data Analysis

For the data analysis, an extracted ion chromatogram (EIC) was used, and the EIC peak area of t-butyl alcohol (EIC: m/z 59.000) that appeared in the relative retention time of 0.48 to 0.56 was observed, where the relative retention time of toluene-d8 was regarded as 1.0. The t-butyl alcohol concentration in terms of toluene-d8 of the 3,5,5-trimethylhexanoic acid vapor was calculated using an equation derived from the calibration curve, "concentration in terms of toluene-d8 (ppb by volume)=$3.49\times10^{-6}\times$EIC peak area", where the sensitivity of the EIC peak of t-butyl alcohol and the sensitivity of the EIC peak of toluene-d8 were supposed to be equal.

Evaluation

Sulfuric Coloring Test

The sulfuric coloring test (sulfuric acid coloring test) of the 3,5,5-trimethylhexanoic acid compositions obtained in Examples 1 to 3 and Comparative Example 1 was conducted in accordance with the method below.

Conditions of Sulfuric Acid Coloring Test

In the sulfuric acid coloring test, 40 mL of the sample was put into a 200-mL Erlenmeyer flask and stirred in an ice bath for three minutes, and 0.2 mL of concentrated sulfuric acid manufactured by KANTO CHEMICAL CO., INC. (Cat. No.: 37390-08, standard: for color test with sulfuric acid) was added to the sample. The mixture was left under stirring conditions in an ice bath for one minute, then placed in a water bath and left still at 20° C. for five minutes. The Hazen unit color number of the sample was measured with a spectrophotometric colorimeter SE7700 manufactured by NIPPON DENSHOKU INDUSTRIES Co., Ltd. In the measurement, the average value of the results of three measurements of the same sample was calculated and used as the score of the Hazen unit color number (APHA).

TABLE 1

| | Example 1 | Example 2 | Example 3 | Comparative Example 1 |
|---|---|---|---|---|
| t-Butyl alcohol concentration in terms of toluene-d8 (ppb by volume) | 185 | 144 | 108 | 317 |
| Sulfuric acid coloring test (APHA) | 32 | 24 | 24 | 94 |

As it is seen from Table 1, a large amount of t-butyl alcohol remained after the conventional purification by distillation, and the existence of the t-butyl alcohol deteriorated the sulfuric acid coloring evaluation of the 3,5,5-trimethylhexanoic acid composition.

On the other hand, the t-butyl alcohol concentrations in terms of toluene-d8 of the 3,5,5-trimethylhexanoic acid compositions obtained in Examples 1 to 3 measured by gas chromatography-olfactometry/mass spectrometry were 200 ppb by volume or less, and it can be seen that the sulfuric acid coloring evaluation thereof was excellent.

INDUSTRIAL APPLICABILITY

According to the present invention, a 3,5,5-trimethylhexanoic acid composition which is excellent in sulfuric acid coloring evaluation, a method for producing the composition and a method for improving sulfuric acid coloring of the composition can be provided. The 3,5,5-trimethylhexanoic acid according to the embodiment (3,5,5-trimethylhexanoic acid) can be used as a raw material of a lubricating oil (for example, a refrigeration oil), metallic soap, a plasticizer, a surfactant, an alkyd resin, a fatty acid chloride, a metal working oil, a cosmetic product or the like.

The invention claimed is:

1. A 3,5,5-trimethylhexanoic acid composition comprising:
3,5,5-trimethylhexanoic acid; and
t-butyl alcohol,
wherein a concentration of the t-butyl alcohol exceeds 0 ppb by volume and is less than or equal to 200 ppb by volume in terms of toluene-d8 measured by a gas chromatography-olfactometry/mass spectrometry.

2. A cosmetic product, wherein the product comprises the 3,5,5-trimethylhexanoic acid composition according to claim 1.

3. A refrigeration oil, wherein the oil comprises the 3,5,5-trimethylhexanoic acid composition according to claim 1.

4. The 3,5,5-trimethylhexanoic acid composition according to claim 1, wherein the t-butyl alcohol concentration is 190 ppb by volume or less.

5. The 3,5,5-trimethylhexanoic acid composition according to claim 1, wherein the t-butyl alcohol concentration is 160 ppb by volume or less.

6. The 3,5,5-trimethylhexanoic acid composition according to claim 1, wherein the t-butyl alcohol concentration is 140 ppb by volume or less.

7. The 3,5,5-trimethylhexanoic acid composition according to claim 1, wherein the composition has a Hazen unit color number of 32 or less as determined by a sulfuric acid coloring test.

8. The 3,5,5-trimethylhexanoic acid composition according to claim 1, wherein the Hazen unit color number is 24 or less as determined by a sulfuric acid coloring test.

9. The 3,5,5-trimethylhexanoic acid composition according to claim 1, wherein the t-butyl alcohol concentration is 190 ppb by volume or less, and wherein the composition has a Hazen unit color number of 32 or less as determined by a sulfuric acid coloring test.

10. The 3,5,5-trimethylhexanoic acid composition according to claim 1, wherein the t-butyl alcohol concentration is 160 ppb by volume or less, and wherein the Hazen unit color number is 24 or less as determined by a sulfuric acid coloring test.

11. The 3,5,5-trimethylhexanoic acid composition according to claim 1, wherein the t-butyl alcohol concentration is 140 ppb by volume or less, and wherein the Hazen unit color number is 24 or less as determined by a sulfuric acid coloring test.

* * * * *